(12) United States Patent
Hu et al.

(10) Patent No.: US 8,916,750 B1
(45) Date of Patent: Dec. 23, 2014

(54) BARLEY ENDOSPERM PROMOTER

(75) Inventors: Gongshe Hu, Pocatello, ID (US); Victor Raboy, American Falls, ID (US)

(73) Assignee: The United States of America, as represented by the Secretary of Agriculture, Washington, DC (US)

(*) Notice: Subject to any disclaimer, the term of this patent is extended or adjusted under 35 U.S.C. 154(b) by 233 days.

(21) Appl. No.: 13/249,192

(22) Filed: Sep. 29, 2011

Related U.S. Application Data

(60) Provisional application No. 61/387,967, filed on Sep. 29, 2010.

(51) Int. Cl.
- *C12N 15/00* (2006.01)
- *A01H 5/00* (2006.01)
- *A01H 5/10* (2006.01)

(52) U.S. Cl.
USPC ......... 800/298; 435/320.1; 435/419; 800/320

(58) Field of Classification Search
None
See application file for complete search history.

(56) References Cited

U.S. PATENT DOCUMENTS 6,867,293 B2 * 3/2005 Andrews et al. ............. 536/23.6

* cited by examiner

*Primary Examiner* — David H Kruse
*Assistant Examiner* — Jason Deveau Rosen
(74) *Attorney, Agent, or Firm* — John D. Fado; Howard Owens

(57) ABSTRACT

Described herein is a seed-enhancing gene promoter in barley (*Hordeum vulgare* L.).

8 Claims, 1 Drawing Sheet

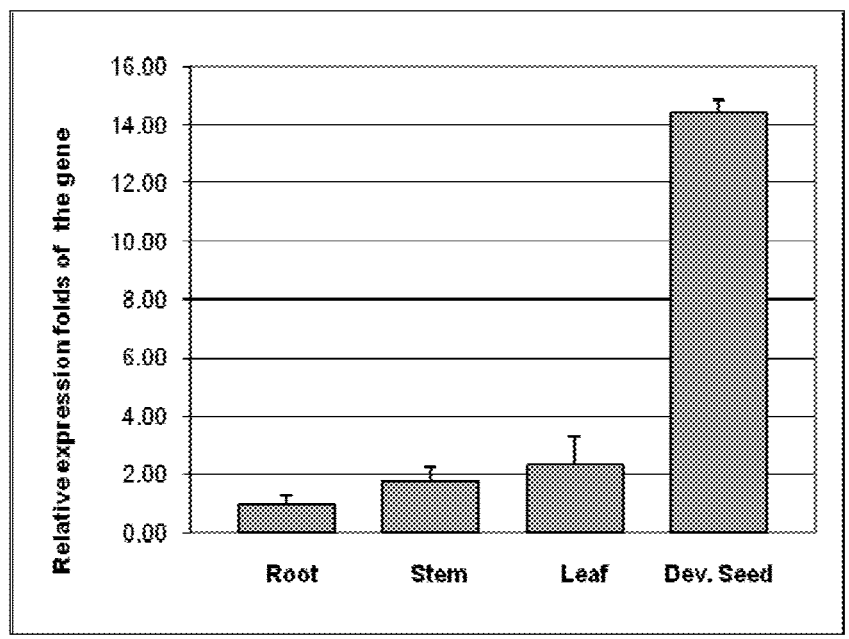

SEQUENCE LISTING

```
<160> NUMBER OF SEQ ID NOS: 1

<210> SEQ ID NO 1
<211> LENGTH: 1413
<212> TYPE: DNA
<213> ORGANISM: Hordeum vulgare
<220> FEATURE:
<221> NAME/KEY: promoter
<222> LOCATION: (1)..(1413)

<400> SEQUENCE: 1
gtttttgttg cttcaacttg ttaacggcgg tcagcctgtt cagcattctc gacgtggttt      60
tgattttgag gatatcccca gttgttttag cgactgtgcc cgggacagtt atgtcatttt     120
aagttttttg tctgtagtaa gatatgtgca tttgatgatt cagaattttg agcattcact     180
```

-continued

```
tgtgagctcg acagttcaga cggtggctgt aatctatgca gattgtagat tttagaaaaa      240
aaattgacaa aaaaaaacta ctacctctgt cacagtttat aaggcacgca cgtgtaccta      300
ggtcgtcaat ttgacttata taaaatatat tgtttaaaat aaaaattata tcattagaaa      360
atagaacatc taaagtttct aatgatatat ttttgtaata tatgcctctc attaagttgg      420
tcaaattgac gacctagata catgtgccgg acttataaac tgaaacggag gtagtacttc      480
atattacttg ttgcagcttt atagcacgat cataggaagt gcagtaacat tttatcaaaa      540
ttccggtaaa tttcggggag atcaaagaca tgctaatgcg ttgcatcaaa gcgagcgagc      600
acctacctca ccgcaggtag gtgggggggtg ggtacagcag ctcctcatga tgaatcacag      660
gtcacgcacg cacgcacgca cgacaagctg atgccggcat gggcatcggc gcgctgtccg      720
tctcactgga accacatgca aacgcccgt ccgcgtggcg tccactcttc ctccacgttt      780
cggcttccct cccgggaatc tgcagcagcc ttccttttc ctccctccgg agtccggatt      840
cctgattcct ccaacaacgc aactggggcg gtagcggtag cggtagcagc tgcagcacta      900
gcgagcgagc gagcggcagc ggcggcgaca cgagagcgcc ggcccgcccc cgccgcgggc      960
tgcagccgcc ctcctctcct ccggccaccg ggaccgcgcc ctggtccgac gccagcgccc     1020
gcgcggctct gctcctcgcc tccgctggta agcacccgcg cccgcctcca ctgctcctct     1080
gggaaacctc cgccgcctcc cgcccgcgcg cgcgcacgcc aactgctcga cggaatgcgg     1140
cgccgaccag agacacaagc tcgcccgctt tctctccaca ttaattccgg ccgcgggctt     1200
ttgctgccgc gtcgagcggc ggagctaacg acaacccgcc cattcccaga tgcacaatca     1260
tcatctgccc agctctgccc accttttatt tatttattta tttttttggct tttccaacaa     1320 ttgccgtctc ggttcctctc ctggatccac tcgtctgatc ccgtgccggc tgcagattct     1380
gggcggagat ggaggccgtg ctgcaggccg gag                                 1413
```

BARLEY ENDOSPERM PROMOTER

RELATED APPLICATIONS

This application is claims benefit of U.S. Provisional Patent Application Ser. No. 61/387,967, filed Sep. 29, 2010 the contents of which are incorporated herein by reference in their entirety.

FIELD OF THE INVENTION

The present invention relates to a seed-enhancing gene promoter isolated from barley (*Hordeum vulgare* L.).

BACKGROUND OF THE INVENTION

Phytic acid, the most abundant "inositol phosphate" (Ins P) in nature, is synthesized in all cells but high rates of synthesis are observed in seeds. In cereals grains phytic acid is synthesized in both the germ/embryo and aleurone. In an experiment searching for the barley Lpa1 gene, Mapping work and genomic characterization in the chromosomal region in Lpa1 mutant, another related gene in phytic acid metabolism, Ins polyphosphate 2-kinase, has been identified. Southern blot analyses indicated the barley genome contains one copy of this gene. Expression patterns of the Ins polyphosphate 2-kinase gene indicate that this gene is constitutively expressed in all tissues but that the promoter has seed-specific or seed-enhancing elements.

SUMMARY OF THE INVENTION

An object of the invention is to provide a seed specific promoter activity in crops of SEQ ID NO: 1 wherein the promoter could be used to drive transgenic expression in seed-enhanced manner in genetic engineering to produce targeted products mainly in seed tissues such as proteins, lipids, fibers et al.

A further embodiment is the use of the promoter to knock-out gene function in more seed-specific manner to manipulate the metabolic pathway for either increasing or decreasing targeted products depending on the particular gene function on the pathway.

BRIEF DESCRIPTION OF THE DRAWINGS

FIG. 1 Shows expression patterns of the Ins polyphosphate 2-kinase gene in different tissue samples. Expression level in developing seeds is at least 7 folds more than any other tissue samples.

DESCRIPTION OF THE INVENTION

The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement.

It is therefore the object of the present invention to provide an seed promoter that allows the genetically engineered production of desired components such as proteins and nucleotide sequences in order to manipulate some targeted metabolic processes in the seed of plants.

Therefore, one subject of the invention is a promoter based on the Ins polyphosphate 2-kinase gene, preferably according to SEQ ID NO:1.

Preferably, the polynucleotide according to the invention may be used for generation of transgenic monocotyledon plants, especially, plants of the Poacceae family, plants of the genus *Triticum, Hordeum, Avena, Secale, Oryza, Zea* or *Aaccharum*; plants of the Musaceae family, plants of the genus *Musa*, plants of the Arecaceae family; plants of the genus *Phoenix, Elaeis* or *Cocos*.

Support for this amendment is found on p. 4, of the specification and originally filed claim 5. Page 4 of the specification lists the crops associated with the monocotyledon plant families (as represented in originally filed claim 5) and included the genus *Hordeum* which is now properly listed as a genus of the family Poacceae (recognized taxonomically as a genus of the family Poacceae and originally set forth in claim 5). Particularly preferred according to the invention are the crops barley, wheat, oat, rye, rice.

Another subject of the invention are polynucleotides that can be obtained by screening a DNA or EST bank with a corresponding gene probe, e.g. consisting of at least 150-200 nucleotides of the polynucleotide according to the invention. Such DNA banks may be readily accessed by a person skilled in the art.

Therefore, according to the invention, a polynucleotide with the biological function of a promoter is provided that achieves a largely seed-specific expression of an operatively linked foreign gene in transgenic plants. In this way, specific polypeptides may be specifically enriched in the seeds.

The term "operatively linked" means that a regulatory sequence such as a promoter controls the expression of a gene.

The term "transgenic plant" relates to plants which have been generated using recombinant genetics and/or microbiological methods, and not by conventional breeding methods, and which contain at least one promoter according to the invention. Methods for generating transgenic plants are described (Tingay S-, McElroy D., Kalla R., Fieg S., Wang M., Thorton S. and Brettel R. (1997): Agrobacterium tumefaciens-mediated barley transformation. Plant Journal 11; 1369-1376; Wan Y. and Lemaux P. (1994): Generation of a large number of independently transformed fertile barley plants. Plant Physiol. 104; 37-48, Stahl R., H. Horvath, J. Van Fleet, M. Voetz, D. von Wettstein & N. Wolf (2002) T-DNA integration into the barley genome from single and double cassette vectors. Proc. Natl. Acad., Sci. USA 99, 2146-2151; Horvath H., J. Huang, 0. T. Wong & D. von Wettstein (2002) Experiences with genetic transformation of barley and characteristics of transgenic plants. In: Barley Science, G. A. Slafer, J. L. Molina-Carro, R, Savin, J. L. Araus & 1. Romagosa eds. The Harworth Press, New York 2002 pp. 143-176.

The term "seedenhanced or seed-specific expression" refers to the expression patterns of the gene that occurres mainly in the filial tissues of cereal speices seed, which includes embryo, scutellum, aleurone, and endosperm, but only residual level may be detected in other tissues and organs of the maternal plant, including root, shoot and seed coat. Most genes are expressed to some extent in all cells of the plant, which is referred to as "constitutive expression", but some genes have induced levels of expression in a given tissue or organ. This induction can be developmentally induced, where such induction is elevated in response to a developmental program. The terms "seed-enhanced" or "seed-specific" expression refer to a pattern of expression that results in elevated levels of expression in the filial tissues of the seed, in comparison with other tissues and organs. This targeted expression is achieved via the promoter sequence that constitutes the 5'-uncoding part of the gene. This promoter when used in an expression vector contruct can drive this seed-enhanced expression of any coding sequence inserted in the vector. Examples of such promoters, their isolation and use are described in U.S. Pat. No. 7,868,156, and include the cotton α-globulin promoter (U.S. Pat. No. 7,626,081), the maize zein promoters (Zhang et al. 2009) and the oleosin (Ole) promoter (GenBank no. BD235503; Shi et al.).

Identification of the barley Ins polyphosphate 2-kinase gene as displaying "seed-enhancing" expression:

Identification of a barley Ins polyphosphate 2-kinase gene by taking advantage of "synteny" between barley and rice and the availability of the rice genome: A Ins polyphosphate 2-kinase gene was identified and characterized", as follows. The molecular markers determined to identify the chromosomal segment containing barley Ins polyphosphate 2-kinase were used to identify the "syntenic" ("related" or "orthologous") chromosomal segment in rice. A rice "bacterial artificial chromosome" (BAC) containing this chromosomal segment was identified, and the "open reading frames", DNA sequences coding proteins, that it contained were evaluated using current database resources. One such gene contained in this chromosome segment was identified: the gene encoding rice 'inositol polyphosphate 2-kinase", subsequently referred to as "2-kinase". This enzyme catalyzes a critical step in phytic acid synthesis. The rice "2-kinase" sequence was then used to identify a barley BAC containing the orthologous barley variant of this gene.

Analysis of the barley genome indicated that it contained only one copy of this gene. The barley 2-kinase sequence was used to design "polymerase chain reaction" (PCR) primers specific for the gene. These PCR primers were then used to determine the "expression profile" of the gene. RNA was isolated from various tissues of the plants and seeds during their growth. "Real-time PCR" (RT-PCR) using the 2-kinase specific primers determined that there was both "constitutive" (continuous background) expression of the 2-kinase gene, and "induced" (elevated) expression during seed development. The 2-kinase gene's 5'-flanking sequence, the sequence immediately "upstream" of the protein coding sequence, contains the promoter sequence. This promoter sequence was obtained from the 2-kinase gene-containing barley BAC using PCR to cover the region between immediate upstream of the 2-kinase and the immediate downstream of 3' region of the gene in front of the 2-kinase."

The promoter could be used to target expression, either for increased expression of a gene or to target down regulation of a second gene, in tissues of the seed. This promoter when used in an expression vector contruct can drive this seed-enhanced expression of any coding sequence inserted in the vector. Examples of utility associated with such promoters to achieve targeted expression of a gene or to target down regulation of a second gene, in tissues of the seed are described and herein incorporated by reference in U.S. Pat. No. 7,868,156, and include the cotton α-globulin promoter (U.S. Pat. No. 7,626, 081), the maize zein promoters (Zhang et al. 2009) and the oleosin (Ole) promoter (GenBank no. BD235503; Shi et al.).

To reach the seed enhanced expression of particular gene, the plasmid vector could be made to contain the promoter sequence and to link the gene sequence at the 3' end of the promoter. For example, it is known that the Cs1F6 gene in cereal is responsible for beta-glucan biosynthesis (Burton et al., 2006), engineering an expression construct carrying the promoter and the Sc1F6 gene is expected to increase the beta-glucan content in the seeds. The similar approach has been successful used in rice genetic engineering to produce Vitamin A (Ye et al., 2000). In the expression cassette, two genes for vitamin-A were constructed under the endosperm-specific rice promoter of glutelin.

A further embodiment is the use of the promoter to knock-out gene function in more seed-specific manner to manipulate the metabolic pathway for either increasing or decreasing targeted products depending on the particular gene function on the pathway. To reach the goal of this application, the anti-sense sequence of the interested gene could be constructed under driving of the promoter. For example, if we want to decrease of beta-glucan content in the cereal grains, a piece of the Cs1F6 gene could be constructed in opposition orientation of the coding direction under the promoter. Expression of antisense Cs1F6 gene sequence under the promoter will interfere the Cs1F6 function to reduce the beta-glucan in the seeds.

What is claimed is:

1. A vector containing a polynucleotide comprising SEQ ID NO: 1 that provides for endosperm-specific expression of an operably linked foreign gene in plants.

2. A transgenic plant comprising (a) the vector according to claim 1, wherein the polynucleotide is stably integrated into the genome of the plant, and (b) a nucleic acid sequence coding for a foreign gene product, which nucleic acid sequence coding for said foreign gene product is operatively linked to the polynucleotide.

3. A transgenic seed obtained from the plant of claim 2, wherein the seed comprises the vector.

4. The transgenic plant according to claim 2, wherein the plant is selected from the group consisting of monocotyledonous plants of the Poaceae family, the Musaceae family, and the Arecaceae family.

5. A transgenic seed obtained from the plant of claim 4, wherein the seed comprises the vector.

6. A transformed plant cell comprising the vector of claim 1 stably integrated into the genome of the plant cell, wherein the vector further comprises a nucleic acid sequence coding for a foreign gene product, which nucleic acid sequence coding for said foreign gene product is operatively linked to the polynucleotide.

7. A transformed plant tissue comprising the vector of claim 1 stably integrated into the genome of the plant tissue, wherein the vector further comprises a nucleic acid sequence coding for a foreign gene product, which nucleic acid sequence coding for said foreign gene product is operatively linked to the polynucleotide.

8. The transgenic plant of claim 2, selected from the group consisting of barley, wheat, oat, rye, rice, corn, and sugarcane.

* * * * *